United States Patent
Op Den Dries et al.

(10) Patent No.: US 6,300,528 B1
(45) Date of Patent: Oct. 9, 2001

(54) METHOD FOR CLEANING REACTORS USED FOR ACID-CATALYZED PRODUCTION OF BISPHENOLS

(75) Inventors: Gerrit Op Den Dries, Bergen op Zoom; Martin Jaco Soeters, Burgh-Haamstede; Marcellinus Adrianus Klaverveld, Oudenbosch; Eduard Hendricus Schlarmann; Guido Theodorus Fridiswidus Maria Van Dooremal, both of Bergen op Zoom, all of (NL)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/542,555

(22) Filed: Apr. 3, 2000

(51) Int. Cl.⁷ .................................................. C07C 39/16
(52) U.S. Cl. ............................................ 568/728; 568/727
(58) Field of Search ...................................... 568/727, 728

(56) References Cited

U.S. PATENT DOCUMENTS

| | | |
|---|---|---|
| 4,107,218 | 8/1978 | Konrad et al. . |
| 4,294,994 | 10/1981 | Li . |
| 5,210,329 | 5/1993 | Gomes de Matos et al. . |
| 5,243,093 | 9/1993 | Kissinger et al. . |
| 5,245,088 | 9/1993 | Fimuro et al. . |
| 5,288,926 | 2/1994 | Patrascu et al. . |
| 5,368,827 | 11/1994 | Moriya et al. . |
| 5,786,522 | 7/1998 | Cipullo . |
| 5,856,589 * | 1/1999 | Cipullo ................................ 568/728 |
| 5,874,644 | 2/1999 | Gammill . |
| 6,011,184 * | 1/2000 | Aarssen ................................ 568/728 |

FOREIGN PATENT DOCUMENTS

99/51558 * 10/1999 (WO) .

* cited by examiner

*Primary Examiner*—Michael L. Shippen
(74) *Attorney, Agent, or Firm*—Oppedahl & Larson LLP

(57) ABSTRACT

Cleaning of a reactor used in the production of bisphenols is enhanced by heating the reactor wall, for example by the introduction of steam into the shell surrounding the reactor. The steam heats the wall which lies between the shell and the interior reaction chamber, and thus facilitates melting/dissolution of bisphenol:phenol adduct that has formed on the wall on the inside of reaction chamber. The steam is introduced for a period of at least 5 minutes, and preferably for a period of from 5 to 60 minutes. In a variation of this method, a solubility-increasing composition is introduced into the reaction chamber to increase the solubility of the bisphenol during the introduction of steam. Suitable solubility-increasing compositions include hydrochloric acid and/or water, or a mixture of acetone and phenol.

5 Claims, 1 Drawing Sheet

METHOD FOR CLEANING REACTORS USED FOR ACID-CATALYZED PRODUCTION OF BISPHENOLS

This application relates to a method for cleaning reactors used for acid-catalyzed production of bisphenols.

BACKGROUND OF THE INVENTION

Bisphenols, and in particular bisphenol A (2,2 bis(p-hydroxyphenyl) propane), have become industrially significant reactants for a number of processes including the preparation of polycarbonates. Bisphenols are prepared on an industrial scale by one of two processes: an acid-catalyzed or HCl process and an ion exchange process, in which an acidic ion exchange resin such as sulfonic acid-substituted polystyrene is employed. In the HCl process, the bisphenol is prepared by condensation of two moles of phenol with one mole of a ketone or aldehyde, for example acetone, in the presence of HCl. Processes for the production and purification of bisphenols are well known, and are described inter alia in U.S. Pat. Nos. 4,107,218; 4,294,994; 5,210,329; 5,243,093; 5,245,088; 5,288,926; 5,368,827; 5,786,522; and 5,874,644.

During the course of producing, bisphenols by this process, the solubility of the product bisphenol is not always high enough for all of the bisphelnol produced to be dissolved. As a result, the bisphenol may crystallize out as a bisphenol-phenol adduct on the inner surface of the reactor. This layer reduces heat exchange efficiency within the reactor, and hence limits reactor temperature control. The result is a lower quality product, and/or reduced plant capacity. Thus, the reactor used in the production of bisphenols needs to be cleaned periodically to remove any build-up of the bisphenol-phenol adduct. In accordance with known methods, this cleaning is done by either filling the reactor with pure phenol or by charging extra water or acid into the reactor. These actions increase the solubility of bisphenol in the mixture and built-up bisphenol-phenol adduct dissolves. Unfortunately, product produced during such cleaning does not meet specifications. This means that the time spent for cleaning is effectively down time for the reactor. There is therefore a need for a method for cleaning reactors used in the production of bisphenols which allows the cleaning to occur without significant production loss, plant instability or quality loss.

SUMMARY OF THE INVENTION

In accordance with the present invention, cleaning of a reactor used in the production of bisphenols is enhanced by heating the reactor wall, for example by the introduction of steam into the shell surrounding the reactor. The steam heats the wall which lies between the shell and the interior reaction chamber, and thus facilitates melting/dissolution of bisphenol:phenol adduct that has formed on the wall on the inside of reaction chamber. The steam is introduced for a period of at least 5 minutes, and preferably for a period of from 5 to 60 minutes.

In a further embodiment of the invention, a solubility-increasing composition is introduced into the reaction chamber to increase the solubility of the bisphenol during the introduction of steam. Suitable solubility-increasing compositions comprise hydrochloric acid and/or water, or a mixture of acetone and phenol.

DETAILED DESCRIPTION OF THE INVENTION

Figure 1:
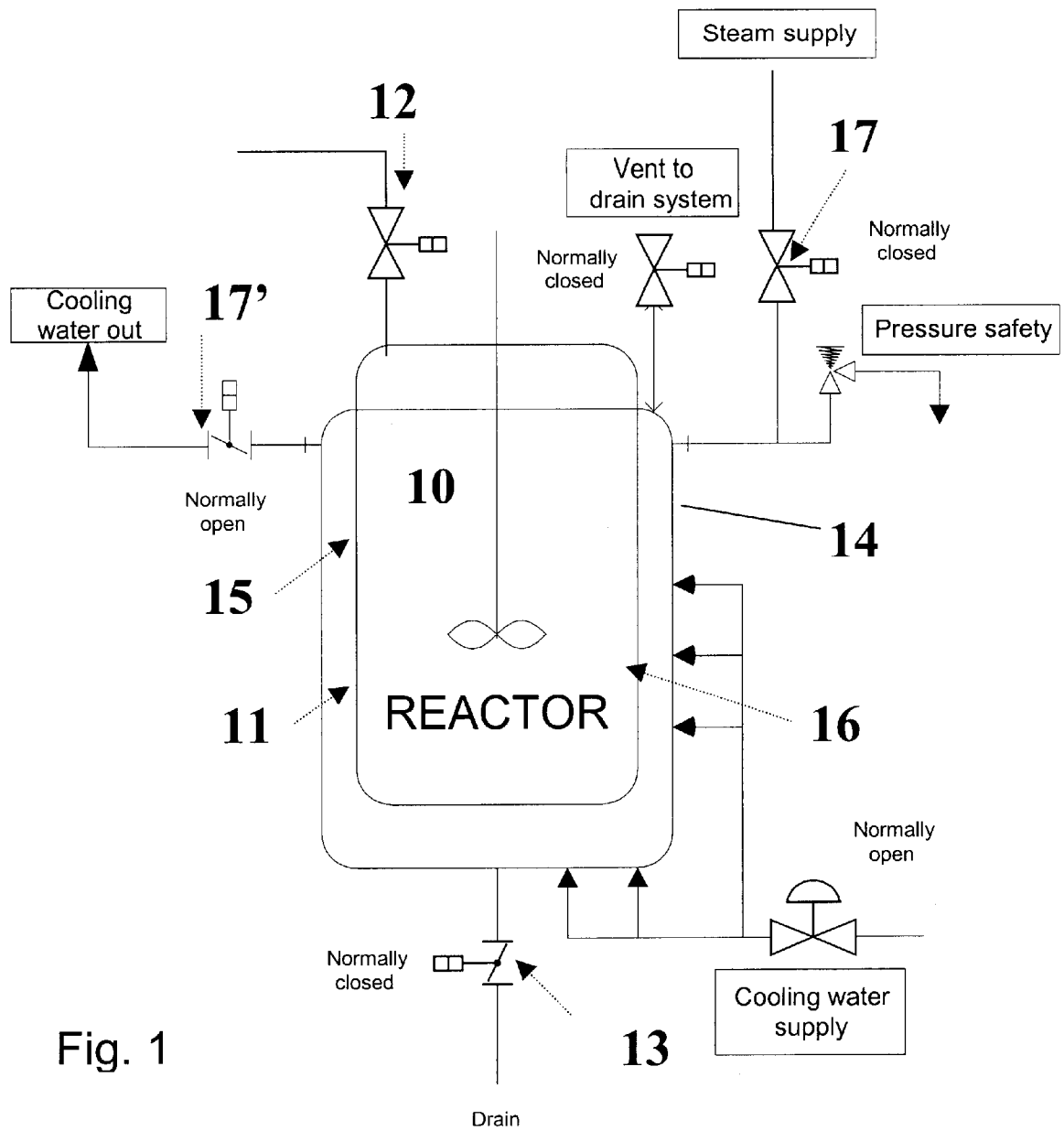
FIG. 1 shows a schematic representation of a reactor which may be cleaned using the method of the invention.

The method of the present invention can be used generally for the cleaning of reactors used in the production of bisphenols. While such reactors may have different sizes and structures, they have certain common features. Thus, a "generic" reactor is depicted in FIG. 1, and the present invention will be described and claimed with respect to the structural features of this reactor. As shown, the reactor has a reaction chamber 10, which is defined by wall 11. Connections 12 and 13 are provided for the introduction and removal of materials from the reaction chamber 10. As is known in the art, the reaction chamber may include baffles, packing materials and the like not shown in FIG. 1.

Surrounding the wall 11 of the reaction chamber 10 is a shell 15 through which heat transfer fluid (e.g. coolant) can be passed. The shell 15 is defined by an exterior wall 14 and an interior wall. The interior wall may be common with wall 11 as shown in FIG. 1, or it may be a separate structure in thermal contact with wall 11 of the reaction chamber. When the reactor is used in the production of bisphenols, a bisphenol:phenol adduct can build up on the interior surface 16 of the reaction chamber 10. This results in a loss of heat transfer efficiency, and thus in a reduction in the efficiency of the production of bisphenol and in the quality of the product.

In accordance with the method of the invention, reactors fouled with a bisphenol:phenol adduct are cleaned by heating the wall surface 16 to a temperature which facilitates dissolution of the bisphenol:phenol adduct. In a specific and economical embodiment of the invention, this heating is accomplished by introducing steam into the shell 15, for example via connector 17. Connector 17' can be used for recovery of steam passed through the shell 15. It will be appreciated however, that other approaches to heating of the surface 16 of wall 11 might also be employed, including circulation of other heat transfer fluids and induction heating of the wall 11 directly. The method of the invention can be utilized in batch, semi-continuous and continuous processes, but it offers the greatest advantages in semi-continuous or continuous operations because it permits cleaning to occur without significant disruption to the operation of the reactor.

When steam is employed as the heat transfer fluid, the steam introduced into the shell may be saturated or unsaturated steam, provided that it has a temperature greater than about 110° C. The amount of steam required will depend on the quality/temperature of the steam used and on various characteristics of the reactor employed, including the volumes of the shell 15 and reaction chamber 10, the thermal transfer characteristics of the reactor/shell interface, and the amount of fouling to be removed. In general, however, steam should be introduced into the shell 15 at a rate sufficient to bring about heating, of the interior surface 16 of the reaction chamber 10 to a temperature of at least 70° C. during the cleaning cycle.

The cleaning cycle time will also vary depending on the characteristics of the reactor noted above, and the temperature and flow rate of the steam employed. For most industrial-scale reactors, the cycle time will be at least 5 minutes. Longer periods of time can be used, and the actual duration of the cleaning cycle represents a balance between the degree of cleaning achieved and the length of the disruption in the manufacturing process. In general, a cleaning cycle with a duration of 5 to 60 minutes is sufficient.

During the steaming operation, normal operating streams of reactants and products can be maintained. The reactor effluent is "normal" before during and after the steaming operation. Thus, the reactor effluent during the cleaning cycle is processed to an HCl recovery facility, phenol distillation facility and ultimately to crystallization and prilling in the normal manner. This makes the method of the invention highly effective for use in semi-continuous or continuous processes, since the disruption in the product production is minimal.

While the introduction of steam into the shell provides substantial cleaning of the surface 16 within the reaction chamber 10, the cleaning efficiency can be enhanced through the introduction of a solubility-increasing composition into the reaction chamber to increase the solubility of the bisphenol during the introduction of steam. As used in the specification and claims of this application, the phrase "during the introduction of steam" does not imply a requirement for absolute synchronicity. Thus, the solubility-increasing composition may be added before the start of steam introduction, somewhat after the start of steam introduction or at the same time as the start of steam introduction. What is important is to have the solubility-increasing composition present in the reaction chamber during at least some of the time that the interior surface 16 is being heated to remove the bisphenol:phenol adduct.

The specific nature of the solubility-increasing composition is not critical, although it is desirable that the composition not interfere with continued reaction to produce bisphenol and does not require expensive recovery/separation efforts. Thus, preferred solubility-increasing compositions are in fact reactants used in the production of bisphenol, employed at different concentrations to drive solubilization of the bisphenol:phenol adduct. Specific examples include HCl, water, combinations of aqueous HCl and water, and mixtures of acetone and phenol. The specific amounts of the solubility-increasing composition employed will depend on the volume of the reaction chamber and the degree of enhancement desired. In general, quantities of 2–5 weight percent of water or acetone are sufficient. Use of additional water or acetone increases the rate at which solubilization occurs, but can also increase the upset to the quality and production rate.

The invention will now be further illustrated with reference to the following, non-limiting example.

EXAMPLE

A reactor of the type shown in FIG. 1 was operated for a period of 9 days under the following reaction conditions: Feedflow 13 m$^3$/h, acetone percentage of 9.5%, temperature 66° C. At the end of this period of time, the reactor was heavily fouled and had to be taken of line for cleaning. The same reactor was then operated in accordance with the invention. The same reaction conditions were employed, except that steam was introduced into shell of the reactor for periods of 10 minutes every day. At the end of 250 days, the reactor was still operating normally. A reactor of the same design was then operated in accordance with a further embodiment of the invention. The same reaction conditions were employed, except that steam was introduced into shell of the reactor for periods of 10 minutes every day and before steam was introduced 200 liter hydrochloric acid was added as a solubility increasing agent. At the end of 100 days, the reactor was still operating normally.

What is claimed is:

1. A method for cleaning a reactor used in the production of bisphenols, wherein the reactor has a reaction chamber and a surrounding shell, said shell being separated from the reaction chamber by an interior wall which allows thermal transfer between the reaction chamber and the shell, and wherein a bisphenol:phenol adduct has formed on a wall portion of the reaction chamber, within the reaction chamber; said method including a descaling step consisting of introducing steam into the shell of the reactor for a period of at least 5 minutes without addition of water to the reaction chamber, whereby heat is transferred from the shell to increase the temperature of the wall-portion of the reaction chamber and facilitate removal of the bisphenol:phenol adduct from the wall portion of the reaction chamber.

2. The method of claim 1, wherein the steam is introduced into the shell for a period of from 5 to 60 minutes.

3. In a method for production of bisphenol by reaction of a phenol and a ketone or aldehyde in the presence of an acid, wherein the reaction is performed in a reaction chamber and a bisphenol:phenol adduct forms on the walls of the reaction chamber, the improvement comprising periodically cleaning the bisphenol:phenol adduct from the walls of the reaction chamber by heating the walls of the reaction chamber while maintaining flows of reactant and product streams into and out of the reaction chamber without the altering the composition of the reactant stream flowing into the reaction chamber.

4. The method of claim 3, wherein the walls of the reaction chamber are heated by introducing steam into a shell surrounding the reaction chamber.

5. The method of claim 4, wherein the steam is introduced for a period of 5 to 60 minutes.

* * * * *